United States Patent
Perälä et al.

(10) Patent No.: US 11,684,269 B2
(45) Date of Patent: Jun. 27, 2023

(54) SENSOR THAT DETECTS A HEART RATE AND/OR A BLOOD OXYGEN CONTENT, AND METHOD OF OPERATING A SENSOR

(71) Applicant: OSRAM Opto Semiconductors GmbH, Regensburg (DE)

(72) Inventors: Mikko Perälä, Tampere (FI); Désirée Queren, Neutraubling (DE); Hubert Halbritter, Dietfurt-Toeging (DE)

(73) Assignee: OSRAM OLED GmbH, Regensburg (DE)

( * ) Notice: Subject to any disclaimer, the term of this patent is extended or adjusted under 35 U.S.C. 154(b) by 682 days.

(21) Appl. No.: 16/479,667

(22) PCT Filed: Jan. 23, 2018

(86) PCT No.: PCT/EP2018/051554
§ 371 (c)(1),
(2) Date: Jul. 22, 2019

(87) PCT Pub. No.: WO2018/138077
PCT Pub. Date: Aug. 2, 2018

(65) Prior Publication Data
US 2020/0345238 A1    Nov. 5, 2020

(30) Foreign Application Priority Data
Jan. 24, 2017 (DE) ............ 10 2017 101 271.0

(51) Int. Cl.
*A61B 5/00* (2006.01)
*A61B 5/0205* (2006.01)
(Continued)

(52) U.S. Cl.
CPC ........ *A61B 5/0205* (2013.01); *A61B 5/14552* (2013.01); *A61B 5/6826* (2013.01);
(Continued)

(58) Field of Classification Search
CPC ............. A61B 5/0205; A61B 5/02427; A61B 5/02433; A61B 5/02416; A61B 5/14551;
(Continued)

(56) References Cited

U.S. PATENT DOCUMENTS 5,299,570 A * 4/1994 Hatschek ........... A61B 5/14552
600/323
2011/0112379 A1    5/2011 Li et al.
(Continued)

FOREIGN PATENT DOCUMENTS

WO    2016/015009 A1    1/2016

*Primary Examiner* — Scott M. Getzow
(74) *Attorney, Agent, or Firm* — DLA Piper LLP (US)

(57) ABSTRACT

A sensor that detects a heart rate and/or a blood oxygen content includes a radiation source and a photodetector, wherein the radiation source includes a light-emitting diode array, the light-emitting diode array includes a plurality of emission regions, the emission regions each include a first light-emitting diode and a second light-emitting diode, the first light-emitting diode includes a first wavelength, the second light-emitting diode includes a second wavelength, and a distance between the first light-emitting diode and the second light-emitting diode within the emission regions is 100 micrometers or less.

16 Claims, 5 Drawing Sheets

(51) Int. Cl.
  *A61B 5/1455* (2006.01)
  *A61B 5/024* (2006.01)
(52) U.S. Cl.
  CPC ........ *A61B 5/7257* (2013.01); *A61B 5/02433* (2013.01); *A61B 2562/0233* (2013.01); *A61B 2562/046* (2013.01)
(58) Field of Classification Search
  CPC . A61B 5/1455; A61B 5/14552; A61B 5/6826; A61B 5/7257; A61B 2562/0233; A61B 2562/046
  See application file for complete search history.

(56) References Cited

U.S. PATENT DOCUMENTS

| | | | | |
|---|---|---|---|---|
| 2011/0205535 | A1* | 8/2011 | Soller | A61B 5/14552 |
| | | | | 356/300 |
| 2012/0248479 | A1* | 10/2012 | Anc | B82Y 20/00 |
| | | | | 977/774 |
| 2015/0018644 | A1* | 1/2015 | Gulati | G01J 3/0218 |
| | | | | 600/316 |
| 2015/0255437 | A1 | 9/2015 | Moosburger | |
| 2016/0345846 | A1 | 12/2016 | Smith et al. | |
| 2017/0000350 | A1 | 1/2017 | Kwon et al. | |
| 2018/0235525 | A1* | 8/2018 | Blanken | A61B 5/14551 |

\* cited by examiner

SENSOR THAT DETECTS A HEART RATE AND/OR A BLOOD OXYGEN CONTENT, AND METHOD OF OPERATING A SENSOR

TECHNICAL FIELD

This disclosure relates to a sensor that detects a heart rate and/or a blood oxygen content as well as a method of operating such a sensor.

BACKGROUND

Sensors that detect a heart rate and/or a blood oxygen content may be constructed by two radiation sources and a photodetector. One radiation source may detect the heart rate, while a second radiation source may detect the blood oxygen content. Such a sensor may comprise, for example, two light-emitting diodes comprising different wavelengths. In that example, the light-emitting diodes are arranged at a distance such that the radiation emitted by the light-emitting diodes acts on different regions of a blood vessel during the detection of the heart rate and/or the blood oxygen content.

There is nonetheless a need to provide an improved sensor that detects a heart rate and/or a blood oxygen content, and a method of operating such an improved sensor.

SUMMARY

We provide a sensor that detects a heart rate and/or a blood oxygen content, including a radiation source and a photodetector, wherein the radiation source includes a light-emitting diode array, the light-emitting diode array includes a plurality of emission regions, the emission regions each include a first light-emitting diode and a second light-emitting diode, the first light-emitting diode includes a first wavelength, the second light-emitting diode includes a second wavelength, and a distance between the first light-emitting diode and the second light-emitting diode within the emission regions is 100 micrometers or less.

We also provide a method of operating a sensor, wherein the sensor includes a radiation source and a photodetector, the radiation source includes a light-emitting diode array, the light-emitting diode array includes a plurality of emission regions, the emission regions each include a first light-emitting diode and a second light-emitting diode, the first light-emitting diode includes a source of green light, the second light-emitting diode includes an infrared source, the distance between the first light-emitting diode and the second light-emitting diode within the emission regions is a maximum of 100 micrometers, the sensor includes a controller, the controller is configured to operate the first light-emitting diodes and the second light-emitting diodes independently of one another, the first light-emitting diodes and the second light-emitting diodes are each operated with a variable voltage oscillating between zero volts and an operating voltage, the oscillating variable frequency of each light-emitting diode includes a dedicated frequency, the signal of the photodetector is divided into individual components on the basis of the dedicated frequencies, and the individual components are assigned to the light-emitting diodes on the basis of the dedicated frequencies.

LIST OF REFERENCE SIGNS

Figure 1:
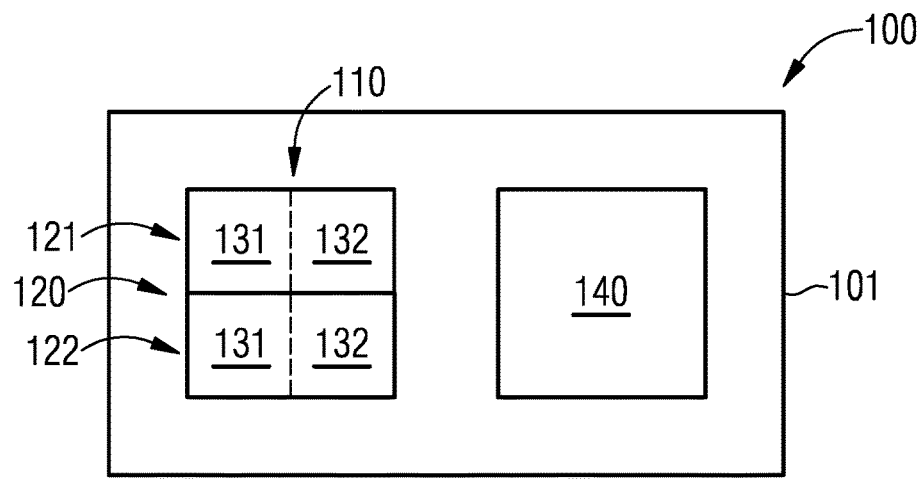
FIG. 1 schematically shows a plan view of a first sensor including a first light-emitting diode array.

100 Sensor
101 Carrier
102 Housing
103 Recess
104 Bearing surface
105 Transparent potting material
110 Radiation source
120 Light-emitting diode array
121 First emission region
122 Second emission region
131 First light-emitting diode
132 Second light-emitting diode
133 Third light-emitting diode
134 First light-emitting diodes chip
135 Second light-emitting diodes chip
136 Third light-emitting diodes chip
137 First conversion element
138 Second conversion element
139 Third conversion element
140 Photodetector
150 Controller
161 First column
162 Second column
163 Third column
164 Fourth column
165 Fifth column
166 Sixth column
167 Row

DETAILED DESCRIPTION

Our sensor that detects a heart rate and/or a blood oxygen content comprises a radiation source and a photodetector. The radiation source comprises a light-emitting diode array comprising a plurality of emission regions. The emission regions each comprise a first light-emitting diode and a second light-emitting diode. The first light-emitting diode comprises a first wavelength, that is to say is configured to emit electromagnetic radiation comprising a first wavelength. The second light-emitting diode comprises a second wavelength, that is to say is configured to emit electromagnetic radiation comprising a second wavelength. Within the emission regions, the distance between the first light-emitting diode and the second light-emitting diode is 100 micrometers or less.

As a result of the distance of a maximum of 100 micrometers, the electromagnetic radiation comprising the first and the second wavelengths is emitted by the radiation source in spatial proximity to one another. Therefore, the probability is high that the light emitted by the first and the second light-emitting diodes within an emission region will penetrate on a similar path into a tissue to be measured and absorptions will take place there at identical molecules within a blood vessel. The measurement accuracy of the sensor that detects a heart rate and/or a blood oxygen content is improved as a result.

The first wavelength may be in the range of 550 to 590 nanometers. The second wavelength may be greater than 800 nanometers. As a result, the first light-emitting diodes emit green light, which is suitable for detecting a heart rate. The second light-emitting diodes emit infrared radiation, which is suitable for determining a blood oxygen content.

The first light-emitting diode may comprise a first conversion element. The second light-emitting diode may comprise a second conversion element. As a result, light comprising a shorter wavelength than the first wavelength may be converted into light of the first wavelength by the first conversion element. Likewise, light comprising a shorter wavelength than the second wavelength may be converted into light of the second wavelength by the second conversion element.

The first and second light-emitting diodes may comprise identical light-emitting diode chips and different conversion elements. Likewise, the first and second light-emitting diodes may comprise different light-emitting diode chips and identical or different conversion elements.

The first conversion element may comprise quantum dots. The second conversion element may comprise quantum dots.

In generating converted light comprising the abovementioned wavelengths by quantum dots, e.g., the materials explained below are possible. For green light of the first wavelength around 570 nanometers, in this example, it is possible to use cadmium selenide quantum dots comprising a diameter of 3.0 to 3.5 nanometers. Alternatively, it is possible to use indium phosphide quantum dots comprising a diameter of 1.8 to 2.2 nanometers for the green light.

Indium arsenide quantum dots comprising a diameter of 3.0 to 6.0 nanometers are possible for the infrared radiation of the second wavelength of greater than 800 nanometers. Alternatively, lead selenide quantum dots comprising a diameter of greater than 5.0 nanometers may be used for the infrared radiation. A further alternative for the infrared radiation is the use of copper indium phosphide quantum dots comprising a diameter of 2.5 to 5.8 nanometers.

The first light-emitting diodes and the second light-emitting diodes may be contacted independently of one another such that each light-emitting diode of the light-emitting diode array is individually drivable. Furthermore, the sensor comprises a controller configured to operate the first and second light-emitting diodes independently of one another. This makes it possible to separate signals of the light-emitting diodes from one another by individual driving of the light-emitting diodes.

The emission regions may comprise a third light-emitting diode, wherein the third light-emitting diode comprises a third wavelength. The third wavelength may be in the range of 640 to 680 nanometers. The third light-emitting diodes thus emit red light. An improved measurement of the blood oxygen content is made possible as a result.

The third light-emitting diode may comprise a third conversion element. The third conversion element may comprise quantum dots.

For the red light in the second wavelength range comprising a wavelength around 660 nanometers, it is possible in this example to use cadmium selenide quantum dots comprising a diameter of 7.5 to 8.5 nanometers. Alternatively, it is possible to use indium phosphide quantum dots comprising a diameter of 2.8 to 3.2 nanometers for the red light.

The photodetector and the radiation source may be arranged within a housing.

The housing may comprise a recess configured to receive a body part. The radiation source and the photodetector may be arranged on different sides of the recess. In this example, the recess may be configured, for example, to receive a finger. By virtue of the fact that radiation source and photodetector are arranged on different sides of the recess, light emitted by the radiation source may pass through the body part located within the recess to the photodetector, wherein absorptions of the radiation relevant to the measurement take place in the body part and the light transmitted through the body part is evaluated by the photodetector. A sensor comprising a good measurement accuracy, in particular for stationary applications, may be achieved as a result.

The housing may comprise a recess, wherein the radiation source and the photodetector are arranged within the recess. The housing may be configured to be arranged on a body part such that the recess faces in the direction of the body part. A flat design of the sensor, in particular for mobile applications, may be achieved as a result.

The light-emitting diode array may comprise a carrier, wherein the light-emitting diodes are arranged in at least four columns and four rows on the carrier. A first column comprises first light-emitting diodes, and a second column comprises second light-emitting diodes. Two emission regions are provided in each row. A space-saving arrangement of the light-emitting diodes and/or of the light-emitting diode array may be achieved as a result.

Third light-emitting diodes may be provided in a third column, wherein the light-emitting diodes may be arranged in at least six columns and at least four rows. As a result, six light-emitting diodes are arranged in each row, in each case three of the light-emitting diodes lying within an emission region.

A sensor that detects a heart rate and/or a blood oxygen content comprising a radiation source and a photodetector, wherein the radiation source comprises a light-emitting diode array comprising a plurality of emission regions, wherein the emission regions each comprise a first light-emitting diode and a second light-emitting diode, wherein the first light-emitting diode comprises a source of green light, the second light-emitting diode comprises an infrared source, and the distance between the first light-emitting diode and the second light-emitting diode within the emission regions is less than 100 micrometers, wherein the sensor comprises a controller, is operated such that the first light-emitting diodes and the second light-emitting diodes are each operated independently of one another with a variable voltage oscillating between zero volts and an operating voltage. In this example, the oscillating variable voltage of each light-emitting diode comprises a dedicated frequency. The signal of the photodetector is divided into individual components on the basis of the dedicated frequencies, wherein the individual components are assigned to the light-emitting diodes on the basis of the dedicated frequencies.

As a result, the light-emitting diodes may be operated and evaluated simultaneously.

The emission regions may comprise third light-emitting diodes that are likewise operated with a variable further voltage oscillating between zero volts and an operating voltage, wherein the further voltage of the third light-emitting diodes in turn comprises a dedicated frequency.

The signal may be divided by Fourier analysis. As a result, a large number of light-emitting diodes of the light-emitting diode array may be operated and evaluated simultaneously.

The above-described properties, features and advantages and the way in which they are achieved will become clearer and more clearly understood in association with the following description of examples explained in greater detail in association with the drawings.

FIG. 1 shows a plan view of a sensor 100. A radiation source 110 and a photodetector 140 are arranged on a carrier 101. The radiation source 110 comprises a light-emitting diode array 120. The light-emitting diode array 120 is subdivided into a first emission region 121 and a second emission region 122, wherein the emission regions each comprise a first light-emitting diode 131 and a second light-emitting diode 132. The light-emitting diode array 120 thus consists of four light-emitting diodes 131, 132 in two emission regions 121, 122. It is also possible to provide more than two emission regions 121, 122 each comprising a first light-emitting diode 131 and a second light-emitting diode 132.

The distance between the first light-emitting diode 131 and the second light-emitting diode 132 within an emission region 121, 122 is in this example 100 micrometers or less. The first light-emitting diodes 131 comprise a first wavelength, while the second light-emitting diodes comprise a second wavelength, which is different than the first wavelength.

In one example, the first wavelength of the first light-emitting diodes 131 is in the range of 550 to 590 nanometers. Light comprising the first wavelength is absorbed by the hemoglobin that occurs in human blood. As a result of a fluctuation of the absorption depending on a quantity of blood in a blood vessel, a heart rate may be determined by the first wavelength of the first light-emitting diodes 131.

In one example, the second wavelength of the second light-emitting diodes 132 is greater than 800 nanometers. The infrared radiation of the second wavelength of the second light-emitting diodes 132 is absorbed by hemoglobin molecules with added oxygen to a greater extent than by hemoglobin molecules without added oxygen. As a result, a blood oxygen content may be measured by the infrared radiation in the second wavelength range of the second light-emitting diodes 132.

Figure 2:
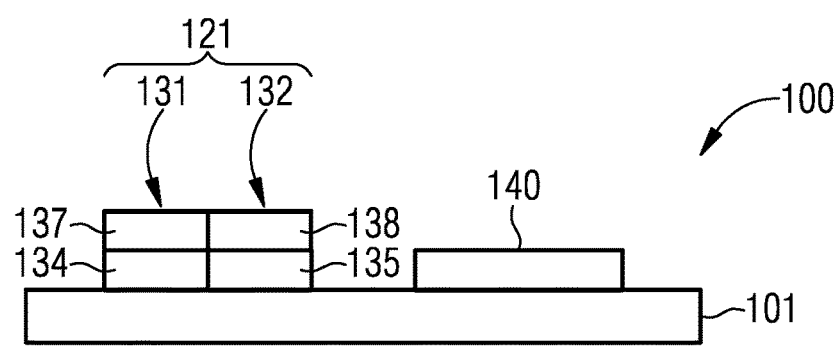
FIG. 2 schematically shows a cross section through the first sensor.

FIG. 2 shows a cross section through a sensor 100, that substantially corresponds to the sensor 100 in FIG. 1. In this example, the cross section extends through the first emission region 121 from FIG. 1. In this example, the first light-emitting diode 131 comprises a first light-emitting diode chip 134 and a first conversion element 137, wherein the first wavelength is generated by virtue of the fact that light comprising a shorter wavelength is emitted by the first light-emitting diode chip 134, which light is then converted into light comprising the first wavelength by the first conversion element 137. The second light-emitting diode 132 comprises a second light-emitting diode chip 135 and a second conversion element 138, wherein the second wavelength is generated by virtue of the fact that light comprising a shorter wavelength is emitted by the second light-emitting diode chip 135, which light is then converted into radiation comprising the first wavelength by the second conversion element 138.

In this example, only the first light-emitting diodes 131 comprise a first conversion element 137 and the second light-emitting diodes 132 consist only of the second light-emitting diode chips 135 without a second conversion element 138 and emit the second wavelength. Alternatively, only the second light-emitting diodes 132 may comprise a second conversion element 138, while the first light-emitting diodes 131 consist only of the first light-emitting diode chips 134 without a first conversion element 137 and emit the second wavelength. Furthermore, first light-emitting diode chips 134 and second light-emitting diode chips 135 may be different from one another or identical.

By way of example, it is possible for the first light-emitting diode chips 134 to emit blue light comprising a wavelength of 405 nanometers and for the first conversion element 137 to convert the blue light into green light comprising a wavelength of 570 nanometers. The second light-emitting diode chips 135 can then, for example, emit red light comprising a wavelength of 670 nanometers and the second conversion element 138 can convert the red light into infrared radiation comprising a wavelength of 950 nanometers.

Alternatively, both the first light-emitting diode chips 134 and the second light-emitting diode chips 135 can emit green light comprising a wavelength of 570 nanometers. The light of the second light-emitting diode chips 135 can then be converted into infrared radiation comprising a wavelength of 950 nanometers by the second conversion element 138, while the first light-emitting diodes 131 do not comprise a first conversion element 137.

In one example, the first conversion element 137 comprises quantum dots. In another example, the second conversion element 138 comprises quantum dots.

For green light of the first wavelength around 570 nanometers, in this example, it is possible to use cadmium selenide quantum dots comprising a diameter of 3.0 to 3.5 nanometers. Alternatively, it is possible to use indium phosphide quantum dots comprising a diameter of 1.8 to 2.2 nanometers for the green light.

Indium arsenide quantum dots comprising a diameter of 3.0 to 6.0 nanometers are possible for the infrared radiation of the second wavelength of greater than 800 nanometers. Alternatively, lead selenide quantum dots comprising a diameter of greater than 5.0 nanometers may be used for the infrared radiation. A further alternative for the infrared radiation is the use of copper indium phosphide quantum dots comprising a diameter of 2.5 to 5.8 nanometers.

Figure 3:
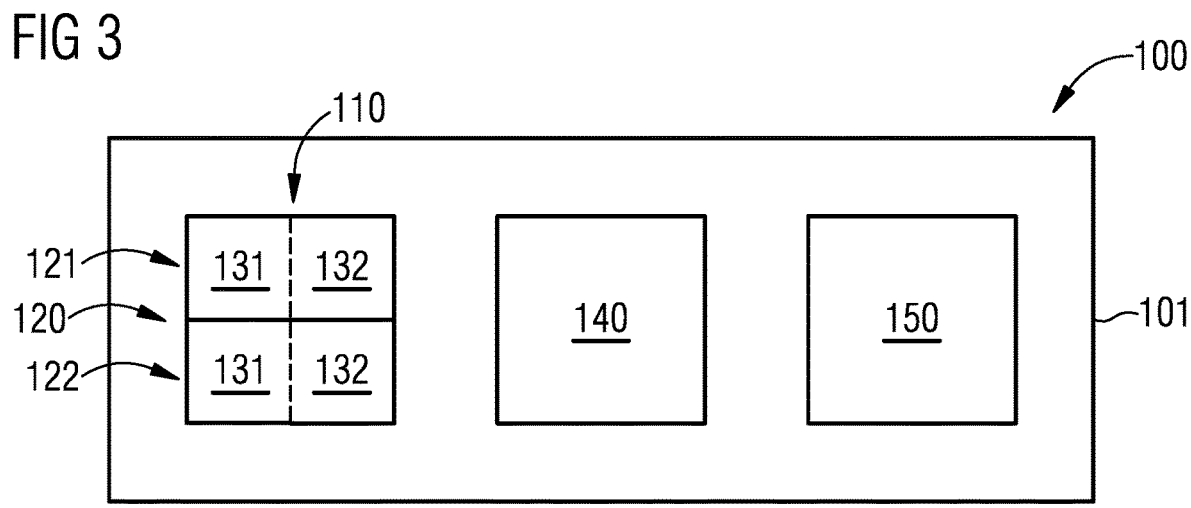
FIG. 3 schematically shows a plan view of a second sensor including the first light-emitting diode array.

FIG. 3 shows a plan view of a sensor 100 that substantially corresponds to the sensor 100 in FIG. 1. The radiation source 110 and the photodetector 140 are constructed analogously to FIG. 1. Furthermore, the carrier 101 comprises a controller 150. The first light-emitting diodes 131 and the second light-emitting diodes 132 are each contacted independently of one another such that each light-emitting diode 131, 132 is individually drivable. The controller 150 is configured to drive and operate the light-emitting diodes individually. Furthermore, the controller 150 may be configured to evaluate a signal of the photodetector 140.

The sensor 100 may be operated such that the first light-emitting diodes 131 and the second light-emitting diodes 132 are each operated independently of one another with a variable voltage oscillating between zero volts and an operating voltage. In this example, the oscillating variable voltage of each light-emitting diode 131, 132 comprises a dedicated frequency. The signal of the photodetector 140 is divided into individual components on the basis of the dedicated frequencies of the light-emitting diodes 131, 132, wherein the individual components are assigned to the light-emitting diodes 131, 132 on the basis of the dedicated frequencies. As a result, the light-emitting diodes 131, 132 may be operated and evaluated simultaneously.

The signals may be divided by Fourier analysis in this example.

Figure 4:
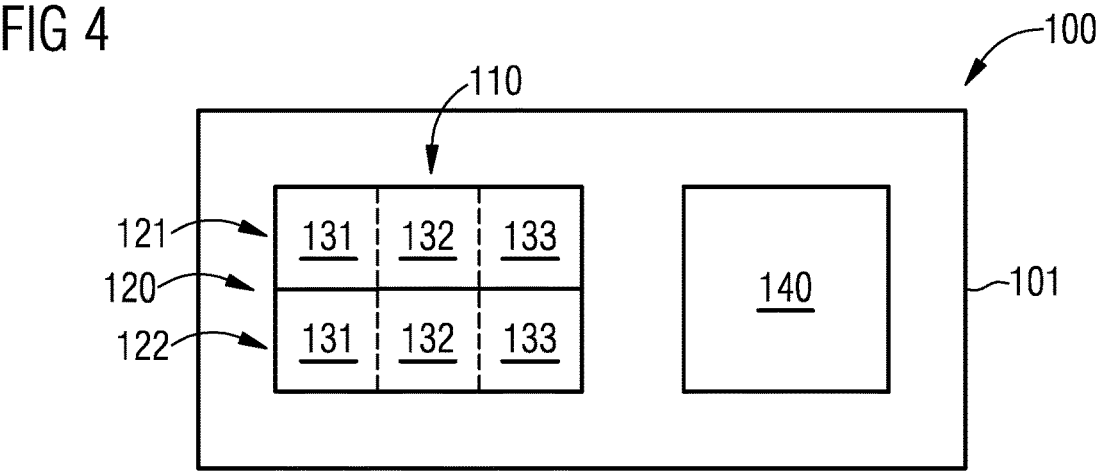
FIG. 4 schematically shows a plan view of a third sensor including a second light-emitting diode array.

FIG. 4 shows a plan view of a further sensor 100 that substantially corresponds to the sensor 100 in FIG. 1. The light-emitting diode array 120 of the radiation source 110 comprises a third light-emitting diode 133 comprising a third wavelength in each emission region 121, 122.

In one example, the third wavelength is in the range of 640 to 680 nanometers. Red light of the third wavelength of the third light-emitting diodes 133 is absorbed by hemoglobin molecules with added oxygen to a lesser extent than by hemoglobin molecules without added oxygen. As a result, measurement of the blood oxygen content may be improved by the red light in the third wavelength range of the third light-emitting diodes 133.

The sensor 100 may be operated such that, in addition to the first light-emitting diodes 131 and the second light-emitting diodes 132, the third light-emitting diodes 133 are also each operated independently of one another with a variable voltage oscillating between zero volts and an operating voltage. In this example, the oscillating variable voltage of each light-emitting diode 131, 132, 133 comprises a dedicated frequency. The signal of the photodetector 140 is divided into individual components on the basis of the dedicated frequencies of the light-emitting diodes 131, 132, 133, wherein the individual components are assigned to the light-emitting diodes 131, 132, 133 on the basis of the dedicated frequencies. As a result, the light-emitting diodes 131, 132, 133 may be operated and evaluated simultaneously.

The signals may be divided by Fourier analysis in this example.

Figure 5:
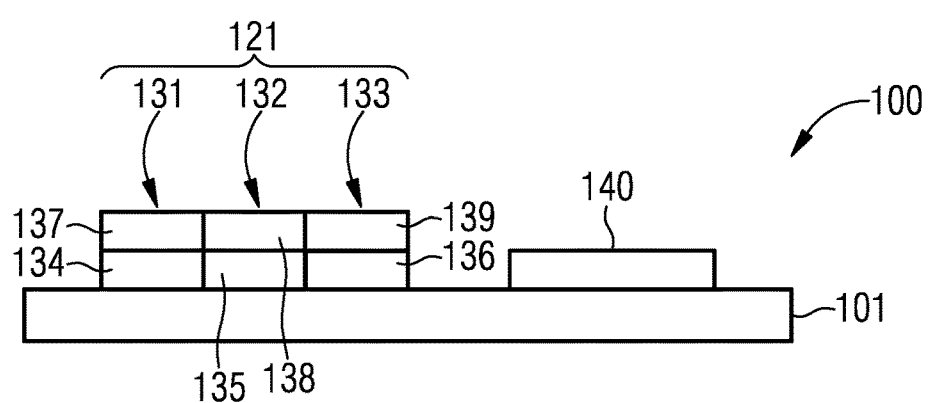
FIG. 5 schematically shows a cross section through a third sensor.

FIG. 5 shows a cross section through the sensor 100 from FIG. 4. In this example, the first light-emitting diode 131 comprises a one first light-emitting diode chip 134 and a first conversion element 137, wherein the first wavelength is generated by the fact that light comprising a shorter wavelength is emitted by the first light-emitting diode chip 134, which light is then converted into light comprising the first wavelength by the first conversion element 137. The second light-emitting diode 132 comprises a second light-emitting diode chip 135 and a second conversion element 138, wherein the second wavelength is generated by the fact that light comprising a shorter wavelength is emitted by the second light-emitting diode chip 135, which light is then converted into radiation comprising the first wavelength by the second conversion element 138. In this example, the third light-emitting diode 133 comprises a third light-emitting diode chip 136 and a third conversion element 139, wherein the third wavelength is generated by the fact that light comprising a shorter wavelength is emitted by the third light-emitting diode chip 137, which light is then converted into light comprising the third wavelength by the third conversion element 139.

In this example, the third light-emitting diode chips 136 may emit blue light comprising a wavelength of 405 nanometers that is converted into red light in the third wavelength range by the third conversion element 139.

Figure 6:
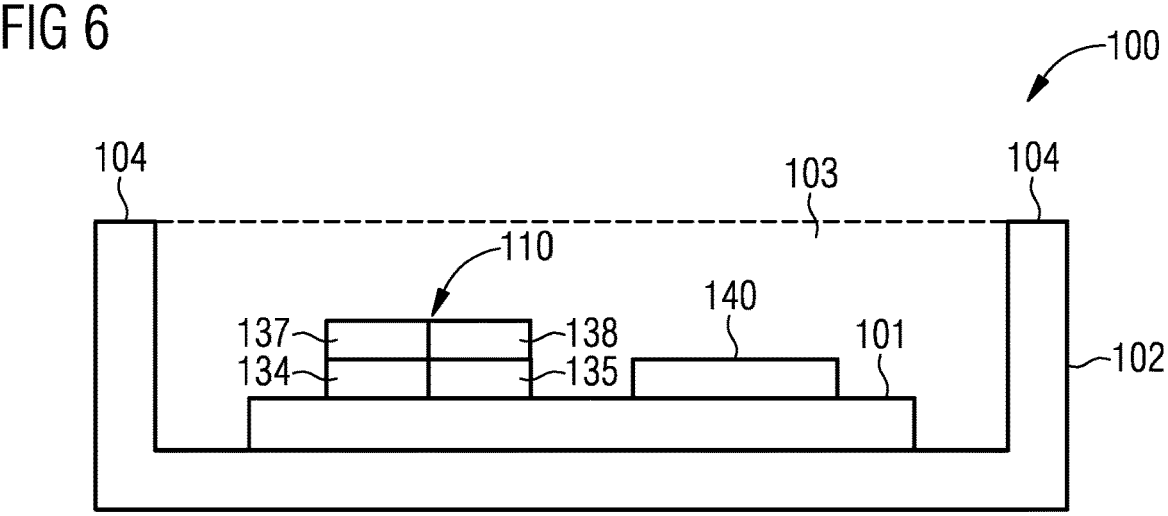
FIG. 6 schematically shows a cross section through a fourth sensor.

FIG. 6 shows a cross section through a further sensor 100. The sensor 100 additionally comprises a housing 102 comprising a recess 103, wherein radiation source 110 and photodetector 140 are arranged within the recess 103 on a carrier 101. An arrangement of radiation source 110 and photodetector 140 within the recess 103 without a carrier 101 is likewise possible.

The housing 102 comprises bearing surfaces 104, wherein the housing 102 may be arranged on a body part such that the housing 102 with the bearing surfaces 104 faces in the direction of the body part. Light emitted by the radiation source 101 may then be scattered and partly absorbed in the body part, wherein the light scattered onto the photodetector 140 may be evaluated.

A dashed line indicates an upper boundary plane of the recess 103 located in a plane with the bearing surfaces 104. The recess 103 may be filled with a transparent material up to the upper boundary plane or be closed with a transparent cover.

Analogously to FIG. 2, one or two of the conversion elements 137, 138, 139 may be absent and the corresponding light-emitting diode chips 134, 135, 136 may emit the corresponding light.

Figure 7:
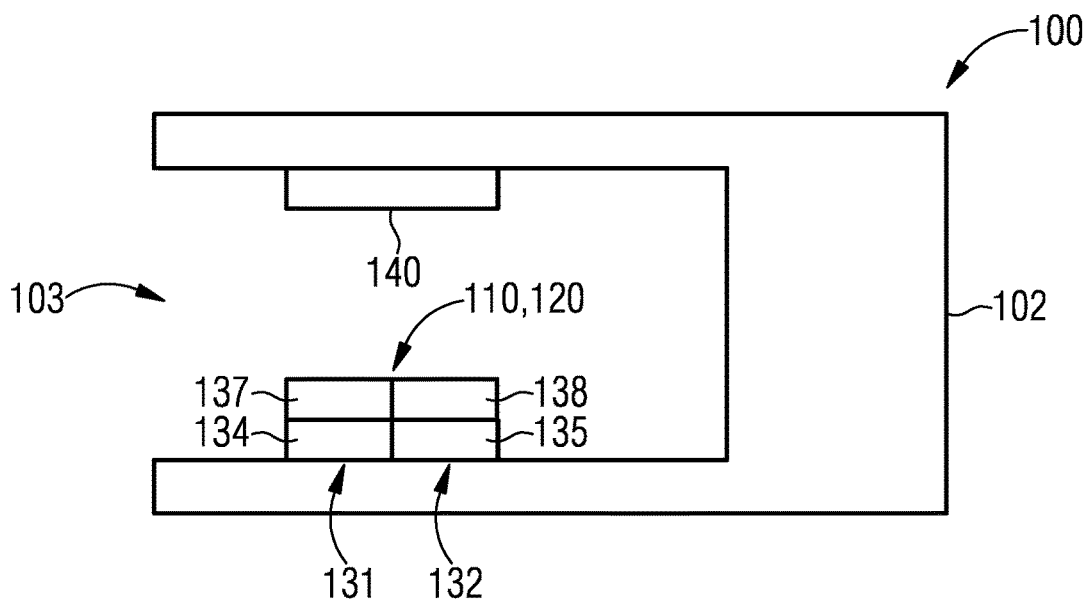
FIG. 7 schematically shows a cross section through a fifth sensor.

FIG. 7 shows a cross section through a further sensor 100 comprising a housing 102 and a recess 103 of the housing 102. The radiation source 110 and the photodetector 140 are arranged on different sides of the recess 103 such that a body part may be received by the recess 103. Light emitted by the radiation source 110 may then transmit through the body part and be partly absorbed in the body part. The transmitted light then impinges on the photodetector 140 and may be evaluated. In this example, the radiation source 110 consists of a light-emitting diode array 120 comprising first light-emitting diodes 131 and second light-emitting diodes 132. The first light-emitting diodes 131 comprise a first light-emitting diode chip 134 with a first conversion element 137. The second light-emitting diodes 132 comprise a second light-emitting diode chip 135 with a second conversion element 138.

Figure 8:
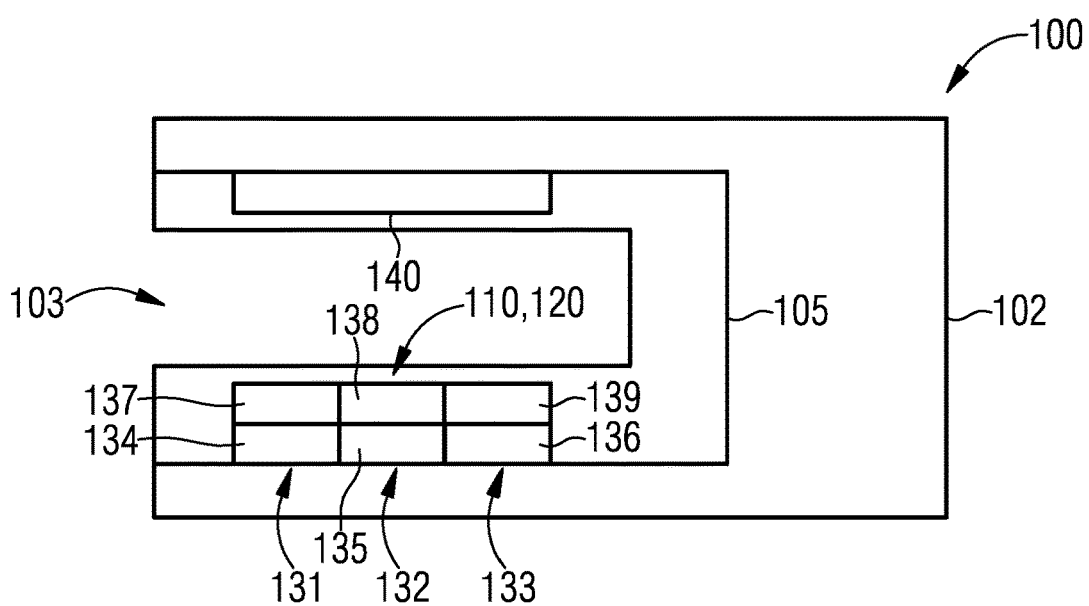
FIG. 8 schematically shows a cross section through a sixth sensor.

FIG. 8 shows a cross section through a further sensor 100 that substantially corresponds to the sensor 100 in FIG. 7. A transparent material 105 is additionally arranged within the recess 103 and surrounds the radiation source 110 and the photodetector 140 and thus protects them against environmental influences. In this example, the radiation source 110 consists of a light-emitting diode array 120 comprising first light-emitting diodes 131, second light-emitting diodes 132 and third light-emitting diodes 133. The first light-emitting diodes 131 comprise a first light-emitting diode chip 134 with a first conversion element 137. The second light-emitting diodes 132 comprise a second light-emitting diode chip 135 with a second conversion element 138. The third light-emitting diodes 133 comprise a third light-emitting diode chip 136 with a third conversion element 139.

Instead of the light-emitting diode arrays 120 in FIGS. 7 and 8, light-emitting diode chips 134, 135, 136 without a corresponding conversion element 137, 138, 139 may also be provided or the light-emitting diode chips 134, 135, 136 may only partly comprise conversion elements 137, 138, 139.

As a result of the small distance between the first light-emitting diode 131 and the second light-emitting diode 132 within an emission region 121, 122, the light emitted by the first light-emitting diodes 131 of an emission region 121, 122 comprises a path through the body part similar to that of the light emitted by second light-emitting diodes 132 of an emission region 121, 122. As a result, the light of an emission region 121, 122 impinges on the same hemoglobin molecules in most situations, such that the measurement of heart rate and blood oxygen content may be carried out in a spatially resolved manner.

FIGS. 9 to 12 each show a plan view of a light-emitting diode array 120, which light-emitting diode arrays may likewise be used in the sensors 100 described above.

Figure 9:
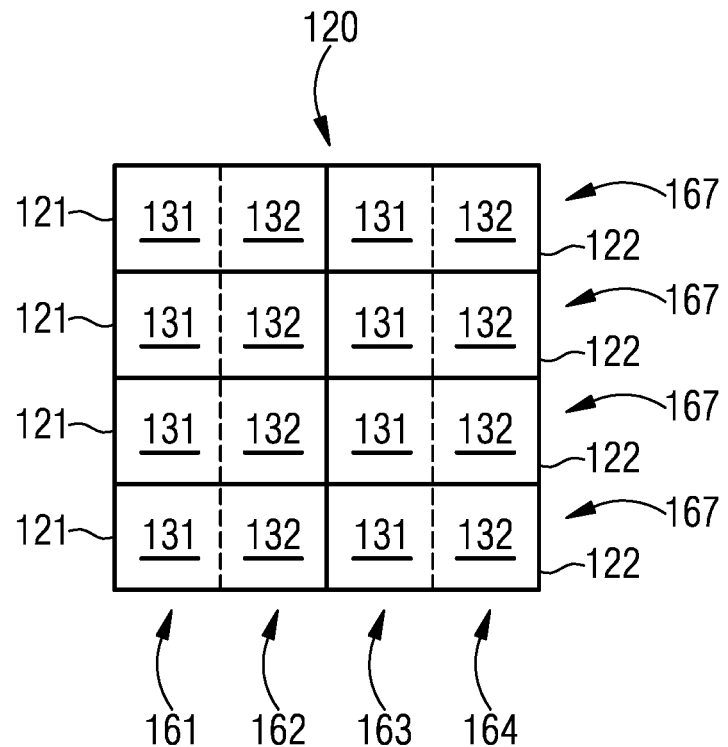
FIG. 9 schematically shows a plan view of a third light-emitting diode array.

In FIG. 9, the light-emitting diode array 120 comprises eight emission regions 121, 122. The light-emitting diode array consists of sixteen light-emitting diodes 131, 132 in four columns 161, 162, 163, 164 and four rows 167. A first emission region 121 and a second emission region 122 each comprising a first light-emitting diode 131 and a second light-emitting diode 132, each arranged in each row 167. First light-emitting diodes 131 are arranged within a first column 161, while second light-emitting diodes 132 are arranged in a second column 162. The light-emitting diodes 131, 132 respectively form the first emission regions 121. First light-emitting diodes 131 are arranged within a third column 163, while second light-emitting diodes 132 are in turn arranged in a fourth column 164. The light-emitting diodes 131, 132 respectively form the second emission regions 122.

Figure 10:
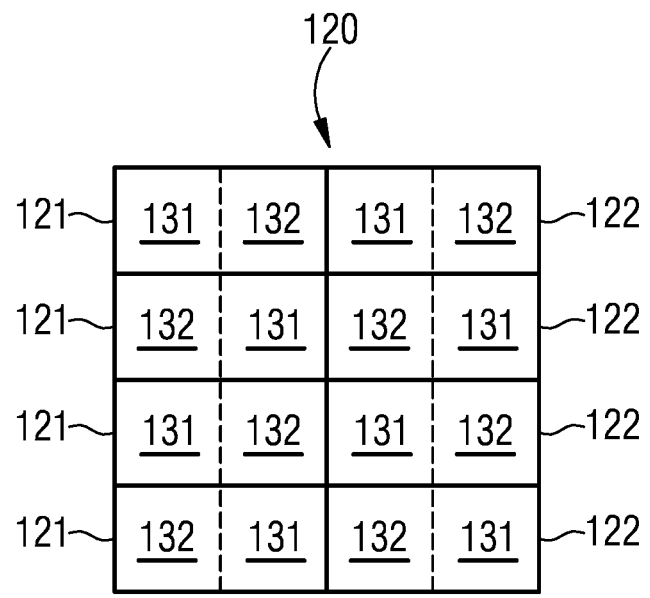
FIG. 10 schematically shows a plan view of a fourth light-emitting diode array.

The light-emitting diode array 120 in FIG. 10 is constructed in a similar manner to the light-emitting diode array 120 in FIG. 9. In FIG. 10, however, the order of the first light-emitting diodes 131 and the second light-emitting diodes 132 has been interchanged in every second one of the rows 167, thus resulting overall in a checkered arrangement of the light-emitting diodes 131, 132.

Figure 11:
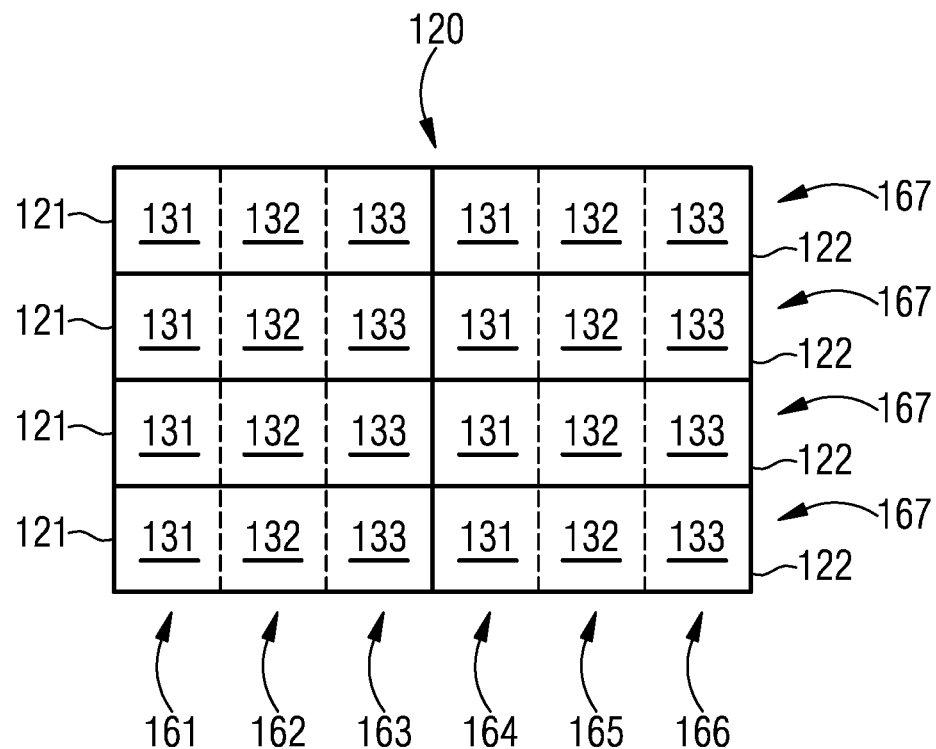
FIG. 11 schematically shows a plan view of a fifth light-emitting diode array.

In FIG. 11, the light-emitting diode array 120 comprises eight emission regions 121, 122. The light-emitting diode array consists of twenty-four light-emitting diodes 131, 132, 133 in six columns 161, 162, 163, 164, 165, 166 and four rows 167. A first emission region 121 and a second emission region 122 each comprising a first light-emitting diode 131, a second light-emitting diode 132 and a third light-emitting diode are each arranged in each row 167. First light-emitting diodes 131 are arranged within a first column 161, while second light-emitting diodes 132 are arranged in a second column 162. Third light-emitting diodes 133 are arranged in a third column 163. The light-emitting diodes 131, 132, 133 respectively form the first emission regions 121. First light-emitting diodes 131 are arranged within a fourth column 164, while second light-emitting diodes 132 are in turn arranged in a fifth column 165. Third light-emitting diodes 133 are arranged in a sixth column 166. The light-emitting diodes 131, 132, 133 respectively form the second emission regions 122.

Figure 12:
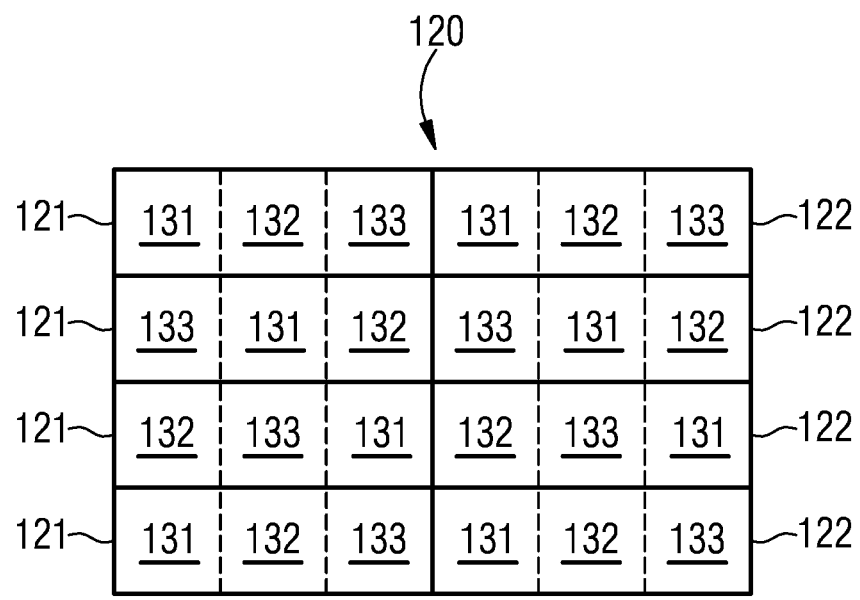
FIG. 12 schematically shows a plan view of a sixth light-emitting diode array.

The light-emitting diode array 120 in FIG. 12 is constructed in a similar manner to the light-emitting diode array 120 in FIG. 11. In this example, a first light-emitting diode 131, a second light-emitting diode 132, a third light-emitting diode 133 and, finally, a first light-emitting diode 131 are arranged within the first column 161. In this example, a second light-emitting diode 132, a third light-emitting diode 133, a first light-emitting diode 131 and, finally, a second light-emitting diode 132 are arranged within the second column 162. In this example, a third light-emitting diode 133, a first light-emitting diode 131, a second light-emitting diode 132 and, finally, a third light-emitting diode 133 are arranged within the third column 163. The fourth column 164 corresponds to the first column 161, the fifth column 165 corresponds to the second column 162, and the sixth column 166 corresponds to the third column 163.

The light-emitting diodes 131, 132, 133 in FIGS. 9 to 12 may be constructed from light-emitting diode chips 134, 135, 136 with or without a corresponding conversion element 137, 138, 139, analogously to the examples described in FIGS. 1 to 8. Furthermore, the light-emitting diode arrays 120 in FIGS. 9 to 12 may also comprise a larger number of light-emitting diodes 131, 132, 133 with an analogous arrangement.

Although our detectors and methods have been more specifically illustrated and described in detail by preferred examples, this disclosure is not restricted by the examples disclosed and other variations may be derived therefrom by those skilled in the art, without departing from the scope of protection of the appended claims.

This application claims priority of DE 10 2017 101 271.0, the subject matter of which is incorporated herein by reference.

The invention claimed is:

1. A method of operating a sensor, wherein the sensor comprises a radiation source and a photodetector, the radiation source comprises a light-emitting diode array, the light-emitting diode array comprises a plurality of emission regions, the emission regions each comprise a first light-emitting diode and a second light-emitting diode, the first light-emitting diode comprises a source of green light, the second light-emitting diode comprises an infrared source, the distance between the first light-emitting diode and the second light-emitting diode within the emission regions is a maximum of 100 micrometers, the sensor comprises a controller, the controller is configured to operate the first light-emitting diodes and the second light-emitting diodes independently of one another, the first light-emitting diodes and the second light-emitting diodes are each operated with a variable voltage oscillating between zero volts and an operating voltage, the oscillating variable frequency of each light-emitting diode comprises a dedicated frequency, the signal of the photodetector is divided into individual components on the basis of the dedicated frequencies, and the individual components are assigned to the light-emitting diodes on the basis of the dedicated frequencies.

2. The method according to claim 1, wherein the emission regions each comprise a third light-emitting diode, the controller is configured to operate the third light-emitting diodes independently of one another and of the first light-emitting diodes and the second light-emitting diodes, the third light-emitting diodes are each operated with a variable further voltage oscillating between zero volts and an operating voltage, and the oscillating variable further voltage of each third light-emitting diode comprises a dedicated frequency.

3. A sensor that detects a heart rate and a blood oxygen content, comprising a radiation source and a photodetector, wherein the radiation source comprises a light-emitting diode array, the light-emitting diode array comprises a plurality of emission regions, the emission regions each comprise a first light-emitting diode and a second light-emitting diode, the first light-emitting diode comprises a first wavelength, the second light-emitting diode comprises a second wavelength, and a distance between the first light-emitting diode and the second light-emitting diode within the emission regions is 100 micrometers or less, and the first wavelength is in a range of 550 to 590 nanometers so that the first light-emitting diode emits green light and the second wavelength is greater than 800 nanometers so that the second light-emitting diode emits infrared radiation, wherein the sensor comprises a controller, the controller is configured to operate the first light-emitting diodes and the second light-emitting diodes independently of one another, the first light-emitting diodes and the second light-emitting diodes are each operated with a variable voltage oscillating between zero volts and an operating voltage, the oscillating variable frequency of each light-emitting diode comprises a dedicated frequency, the signal of the photodetector is divided into individual components on the basis of the dedicated frequencies, and the individual components are assigned to the light-emitting diodes on the basis of the dedicated frequencies.

4. The sensor according to claim 3, wherein at least one of the first light-emitting diode comprises a first conversion element and the second light-emitting diode comprises a second conversion element.

5. The sensor according to claim 4, wherein at least one of the first conversion element and the second conversion element comprise(s) quantum dots.

6. The sensor according to claim 5, wherein the first wavelength is around 570 nanometers, and the quantum dots of the first conversion element are cadmium selenide quantum dots comprising a diameter of 3.0 to 3.5 nanometers or indium phosphide quantum dots comprising a diameter of 1.8 to 2.2 nanometers for the green light.

7. The sensor according to claim 5, wherein the quantum dots of the second conversion element are indium arsenide quantum dots comprising a diameter of 3.0 to 6.0 nanometers or lead selenide quantum dots comprising a diameter of greater than 5.0 nanometers or copper indium phosphide quantum dots comprising a diameter of 2.5 to 5.8 nanometers for the infrared radiation.

8. The sensor according to claim 3, wherein the emission regions comprise a third light-emitting diode, and the third light-emitting diode comprises a third wavelength.

9. The sensor according to claim 8, wherein the third wavelength is in a range of 640 to 680 nanometers.

10. The sensor according to claim 3, wherein 1) the sensor comprises a housing, and the radiation source and the photodetector are arranged within the housing, 2) the housing comprises a recess, the recess is configured to receive a body part or a finger, and 3) the radiation source and the photodetector are arranged on different sides of the recess.

11. The sensor according to claim 3, wherein 1) the sensor comprises a housing, and the radiation source and the photodetector are arranged within the housing, 2) the housing comprises a recess, the radiation source and the photodetector are arranged within the recess, and 3) the housing with the recess may be arranged on a body part such that the recess faces in the direction of the body part.

12. The sensor according to claim 3, wherein the light-emitting diode array comprises light-emitting diodes on a carrier, the light-emitting diodes are arranged in at least four columns and at least four rows on the carrier, a first column comprises first light-emitting diodes, a second column comprises second light-emitting diodes and two emission regions are provided in each row.

13. The sensor according to claim 12, wherein third light-emitting diodes are provided in a third column, and the light-emitting diodes are arranged in at least six columns and at least four rows.

14. The sensor according to claim 3, wherein the light-emitting diode array is subdivided into a first emission region and a second emission region.

15. The sensor according to claim 3, wherein the light-emitting diode array comprises eight emission regions, the light-emitting diode array consists of sixteen light-emitting diodes in four columns and four rows, a first emission region and a second emission region each comprising a first light-emitting diode and a second light-emitting diode are each arranged in each row, first light-emitting diodes are arranged within a first column, while second light-emitting diodes are arranged in a second column, said light-emitting diodes respectively forming the first emission regions, and first light-emitting diodes are arranged within a third column, while second light-emitting diodes are in turn arranged in a fourth column, said light-emitting diodes respectively forming the second emission regions.

16. The sensor according to claim 3, wherein the light-emitting diode array comprises eight emission regions, the light-emitting diode array consists of sixteen light-emitting diodes in four columns and four rows, a first emission region and a second emission region each comprising a first light-emitting diode and a second light-emitting diode are each arranged in each row, and the order of the first light-emitting diodes and the second light-emitting diodes is interchanged in every second one of the rows, thus resulting overall in a checkered arrangement of the light-emitting diodes.

* * * * *